(12) United States Patent
Stepankova et al.

(10) Patent No.: US 7,544,840 B2
(45) Date of Patent: Jun. 9, 2009

(54) METHOD OF PRODUCTION OF (−)-(S)-3-[1-(DIMETHYLAMINO)ETHYL] PHENYL-N-ETHYL-N-METHYLCARBAMATE

(75) Inventors: Hana Stepankova, Cesky Brod (CZ); Josef Hajicek, Praha 2 (CZ); Stanislav Simek, Praha 10 (CZ)

(73) Assignee: Zentiva, a.s. (CZ)

( * ) Notice: Subject to any disclaimer, the term of this patent is extended or adjusted under 35 U.S.C. 154(b) by 630 days.

(21) Appl. No.: 10/523,927

(22) PCT Filed: Oct. 21, 2003

(86) PCT No.: PCT/CZ03/00058

§ 371 (c)(1), (2), (4) Date: Feb. 7, 2005

(87) PCT Pub. No.: WO2004/037771

PCT Pub. Date: May 6, 2004

(65) Prior Publication Data

US 2006/0122417 A1    Jun. 8, 2006

(30) Foreign Application Priority Data

Oct. 24, 2002  (CZ) .......................... PV 2002-3555

(51) Int. Cl.
*C07C 269/00* (2006.01)
(52) U.S. Cl. .................. 564/303; 564/304; 564/305
(58) Field of Classification Search .................. 560/136
See application file for complete search history.

(56) References Cited

U.S. PATENT DOCUMENTS 5,602,176 A    2/1997    Enz

OTHER PUBLICATIONS

Grazyna Ciszewska, Heidi Pfefferkoru, Y.S.Tang, Lawrence Jones, Richard Tarapata and Ustun B. Sunay Synthesis of Tritium, Deuterium, a . . . an Investigational Drug for the treatment of Alzheimer's Disease: Journal of Labelled Compounds and Radiopharmaceuticals, vol. 39, No. 8, pp. 651-668.*
Joseph McL. MacDonald and Edgar Stedman The Resolution of alpha-m-hydroxyphenylethyl-methylamine and the preparation of d- and I-miotine (methylurethanes of d- and I-alpha-m-hydroxphenyl-ethyldimethylamine), J. Chem. Soc. pp. 2513-2519.*
Bhattacharyya S., "Reductive Alkylations of Dimethylamine Using Titanium (IV) Isopropoxide and Sodium Borohydride; An Efficient, Safe and Convenient Method for the Synthesis of N,N-Dimethylated Tertiary Amines", J. Org. Chem., 1995, 60, 4928-4929.*
Chen, Chung-Pin et al. "A General Enantioselective Synthesis of alpha-Arylethylamines", Tetrahedron Letters, vol. 32, No. 49, pp. 7175-7178, XP009025296 1991.

Ciszewska, Grazyna et al. "Synthesis of Tritium, Deuterium, and Carbon-14 Labeled (S)-N-Ethyl-N-methyl-3-[1-(dimethylamino)ethyl]carbamic acid, phenyl ester, (L)-2,3-dihydroxbutanedioic acid salt (SDZ ENA 713 hta), an Investigational Drug for the Treatment of Alzheimer's Disease", Journal of Labelled Compounds and Radiopharmaceuticals, vol. 39, No. 8, pp. 651-668, XP002269029 1997.
MacDonald, Joseph McL. et al. "The Resolution of alpha-m-Hydroxyphenylethyl-methylamine and the Preparation of d-and I-Miotine (Methylurethanes of d- and I-alpha-m-Hydroxphenyl-ethyldimethylamine)", J. Chem. Soc, pp. 2513-2519, XP009034872 1932.

* cited by examiner

Primary Examiner—Yevegeny Valenrod
(74) Attorney, Agent, or Firm—Oblon, Spivak, McClelland, Maier & Neustadt, P.C.

(57) ABSTRACT

The compound of formula (III), optionally its alkaline salt, is reacted with a compound of formula VII, wherein X is a leaving group, resulting in (S)-rivastigmine of formula II, which is then optionally converted into (S)-rivastigmine hydrogentartrade of formula I.

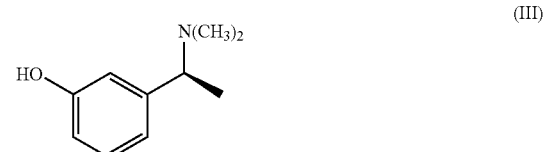

(III)

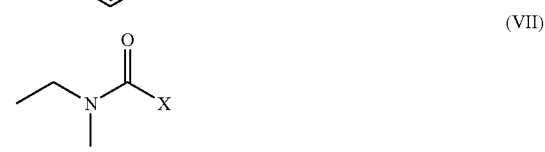

(VII)

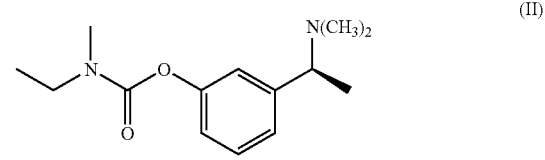

(II)

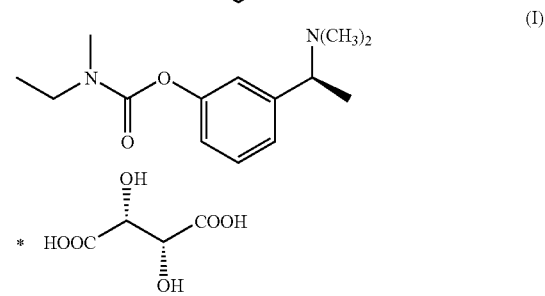

(I)

11 Claims, No Drawings

METHOD OF PRODUCTION OF (−)-(S)-3-[1-(DIMETHYLAMINO)ETHYL] PHENYL-N-ETHYL-N-METHYLCARBAMATE

TECHNICAL FIELD

The invention concerns a method of production of (−)-(S)-3-[1-(dimethylamino)ethyl]phenyl-N-ethyl-N-methylcarbamate and of its hydrogentartrate.

BACKGROUND ART (−)-(S)-3-[1-(dimethylamino)ethyl]phenyl-N-ethyl-N-methylcarbamate tartrate of formula I

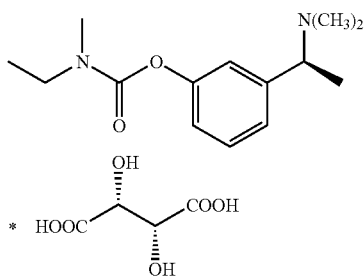

known under the INN name rivastigmine, is described in CS patent application No. PV 1991-4110 as a substance that induces selective inhibition of acetylcholinesterase activity in the brain. This quality along with good tolerance by the human organism, an option to serve in the form of tablets (oral efficiency) and a long-term effect predestines rivastigmine for treatment of disorders associated with the cholinergic system disorder—especially of Alzheimer's disease.

Racemic 3-[1-(dimethylamino)ethyl]phenyl-N-ethyl-N-methylcarbamate (hereinafter racemic rivastigmine), as a substance with a possible activity against Alzheimer's disease, was described in EP patent 193 926. The method of its production was based on reaction of m-hydroxyphenylethyldimethylamine of formula IV

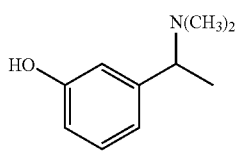

with a carbamoylhalide of formula VI

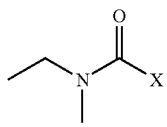

wherein X represents a leaving group.

Methods for producing these racemic intermediates were described in earlier literature, but no possibility of converting the same into optically active enantiomers is mentioned anywhere.

In the cited CS application PV 1991-4110, it is demonstrated using both "in vitro" and "in vivo" experiments that the optically active (S)-isomer is a much more effective and selective inhibitor of acetylcholinesterase than a racemic mixture of the two isomers.

In the cited application, there is described a method of preparation of rivastigmine from the racemic mixture consisting in preparation of diastereoisomeric salts with (+)-O,O-di-(p-toluyl)-D-tartaric acid and their separation by crystallization. The (S)-enantiomer of rivastigmine was released from the obtained salt with a sodium hydroxide solution.

The basic technological disadvantage of this procedure is that optical resolution is performed only in the final stage of synthesis. This means that at least 50% of the prepared racemic rivastigmine (i.e. the (R)-enantiomer)) represents a useless waste; in fact, this waste is much bigger since optical resolution never separates enantiomers quantitatively. This makes the total yield of the synthesis low and the whole process is economically disadvantageous. Another drawback consists in distribution of the losses into individual steps. In general, the losses in a more advanced intermediate are more cost consuming than those in the initial steps.

As it has turned out in testing said procedure, resolution does not result in achieving satisfactory optical purity and the substance has to be additionally recrystallized (cf. Reference Example 1). The necessity of using the expensive and carcinogenic substance of formula VII (mostly specifically N-ethyl-N-methylcarbamoyl chloride) in an about 300% excess is another drawback.

Resolution in an earlier stage of the synthesis appears, at first sight, as desirable, but far from being feasible. There remains the question whether it is possible to obtain enantiomerically pure intermediates and, especially, whether these products can be used for further synthesis without being subject to racemization. The necessity of recrystallization would cast doubts on advantageousness of such procedure.

It has now turned out that optically resolving the intermediate products (i.e. performing the operation in an earlier stage of production) and performing the final step with an optically active substance, permits to obtain a very good yield of (S)-rivastigmine with retaining high analytic purity.

DISCLOSURE OF INVENTION

The present invention consists in a method of production of (−)-(S)-3-[1-(dimethylamino)ethyl]phenyl-N-ethyl-N-methylcarbamate (rivastigmine) of formula II

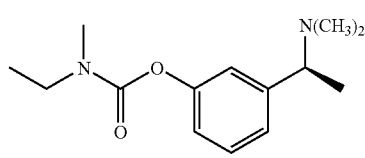

or of its hydrogentartrate of formula I

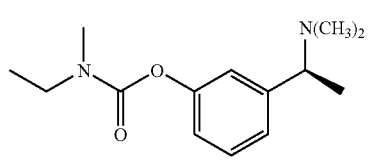

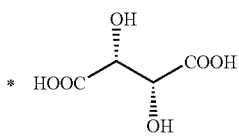

in which methoxyacetophenone of formula VI

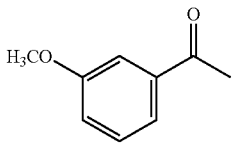

is reductively aminated to the compound of formula V

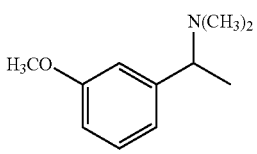

which is thereafter O-dealkylated to the racemic amine of formula IV

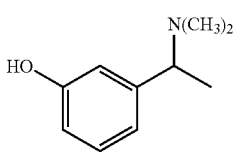

which is further resolved by reacting with an optically active acid, whereafter the desired respective diastereoisomer is crystallized and finally converted into the compound of formula III

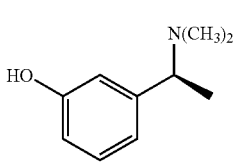

which, in turn, is reacted, optionally in the form of its alkali salt, with a compound of formula VII

wherein X is a leaving group.

The resulting compound of formula II

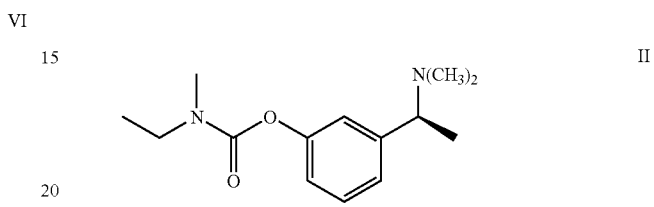

is converted, by reacting with tartaric acid, into the respective salt of formula I.

Advantageously, the phenol of formula III is converted with a strong base in an inert solvent into the phenolate and it is reacted with the carbamoylhalide of formula VII.

As the strong base, hydrides of alkali metals, such as sodium hydride, or alkyl lithium compounds such as butyl lithium, can be used. The inert solvent is preferably chosen from the group of dialkyl ethers such as tetrahydrofuran or 1,2-dimethoxyethan.

The reductive amination is carried out by means of dimethylamine or its hydrochloride and a reduction agent, usually a hydride such as sodium borohydride.

The O-dealkylation agents can be selected from among strong acids, such as for example hydrobromic acid, or from among boron halides, such as boron bromide.

The racemic amine of formula IV is preferably resolved by reacting with (S)-(+)-camphor-10-sulfonic acid.

The obtained desired respective diastereoisomer can further be re-crystallized, preferably from ethylacetate, optionally in admixture with ethanol.

As is demonstrated in the examples of especially preferred embodiments, the present method makes it possible for obtaining the product of formula I in an especially high optical purity. A reproduction of the method known so far, even with recrystallization, has not resulted in obtaining such high optical purity.

It further results from comparison that use of the optically active compound of formula III results in lowering of the consumption of the expensive and carcinogenic N-ethyl-N-methylcarbamoylchloride (corresponding to general formula VII for X=Cl) by ⅔.

EXAMPLES

The subject matter of the invention is demonstrated in more detail in the following examples.

Example 1

Preparation of (S)-(−)-rivastigmine hydrogentartrate (I) (cf. Scheme 1)

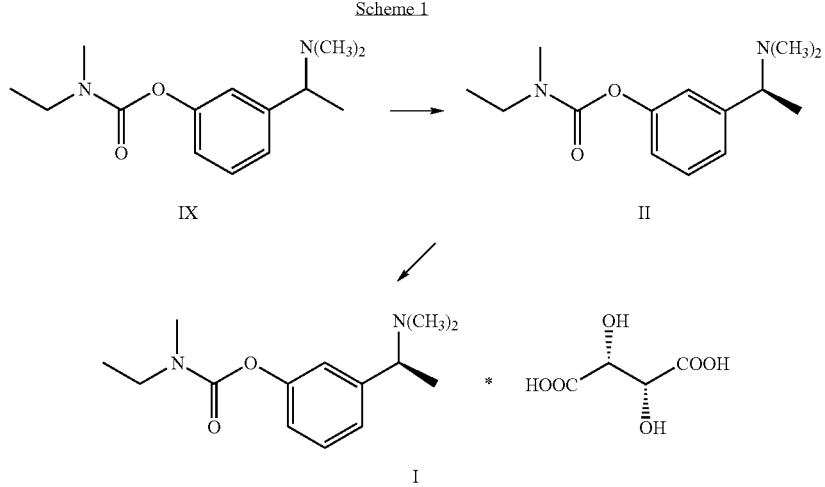

Resolving Racemic Compound (IX) with (+)-O,O'-ditoluyltartaric Acid 49.6 g of racemic compound (IX) are dissolved in 100 ml of methanol and a solution of 75.8 g of (+)-O,O'-ditoluyltartaric acid in 200 ml of methanol is added to the solution. 150 ml of water are added stepwise to the clear solution, which is being mixed. The solution becomes turbid and starts to crystallize under cold conditions. 81.3 g of the desired salt in the form of white crystals with m.p.=145-147° C. are obtained. The mentioned amount of the first fraction of crystals is recrystallized from a mixture of 200 ml of methanol and 100 ml of water. The second fraction of crystals (49.6 g, m.p.=155-156° C.) is obtained which is again recrystallized from the mixture (methanol:water (2:1), 200 ml). 39.0 g of the third fraction is obtained with m.p.=159-162° C. It is recrystallized from 150 ml of the mentioned mixture of solvents and the fourth final fraction of crystals is isolated (33.0 g, m.p.=156-7° C.), which is 26.9% of the theoretical yield, $[\alpha]_D$=+78.5° (c=1, ethanol).

Releasing the Base (II)

The salt of S-(−)-rivastigmine (II) with (+)-O,O'-ditoluyltartaric acid (33.0 g) is slowly added to the well mixed mixture of 150 ml of dichloromethane and 150 ml of 1N NaOH solution. After all the solids are dissolved, the layers are separated; the dichloromethane layer is extracted twice with 100 ml of water, dried with magnesium sulfate. The solvent is evaporated in vacuo and the evaporation residue is distilled under vacuum (b.p.=135-8° C., 40 Pa). 10.72 g of a colorless oil are obtained, which is 85% of the theoretical yield ($[\alpha]_D$=−24.5°; c=3.5, methanol).

Preparation of (S)-(+)-rivastigmine Hydrogentartrate (I)

8.86 g of the base (II) and 5.31 g of L-(+)-tartaric acid are dissolved under warm conditions and stirring in 20 ml of ethanol and the clear solution is precipitated with addition of ethylacetate (250 ml). The resulting mixture is left to cool down to +5° C. The precipitated crystals are sucked away and washed with ethylacetate. 9.7 g of desired rivastigmine hydrogentartrate (I) results (i.e., 68.4% of the theoretical yield) with m.p.=124-126° C. The contents of the undesired (R)-enantiomer in this fraction was 1% (as determined by capillary electrophoresis).

0.3 g of the hydrogentartrate were recrystallized from a mixture ethanol/ethylacetate in the above specified manner and 0.24 g of a recrystallized fraction (I) were obtained (80%). The contents of the undesired (R)-enantiomer has decreased to 0.69% (capillary electrophoresis).

A total yield, based on the starting material (IV), of 12.5% has been obtained.

Example 2

Preparation of (S)-(+)-rivastigmine hydrogentartrate (I) (cf. Scheme 2)

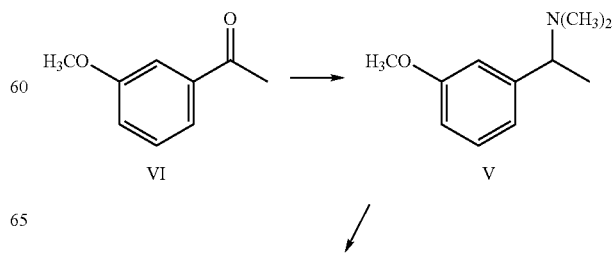

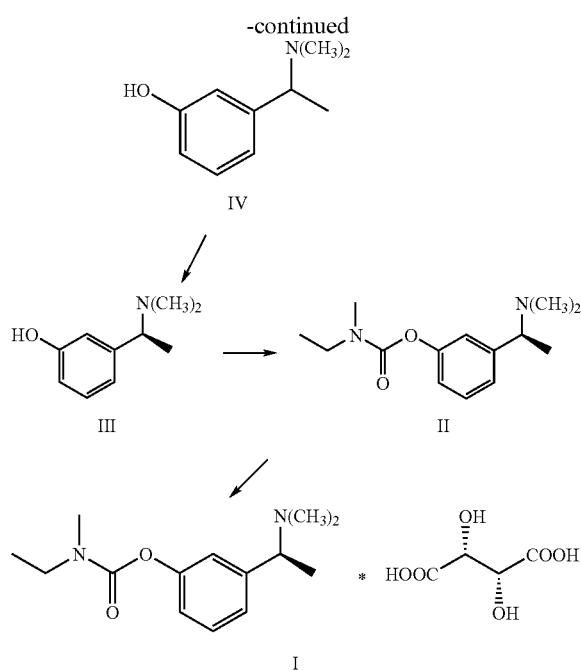

Preparation of [1-(3-methoxyphenyl)ethyl]dimethylamine (V) According to Literature 2

0.5 l of titanic isopropoxide is slowly (5 minutes) added under inert conditions (N$_2$, argon) to a solution of 75.5 g of dimethylamine in 1.5 l of ethanol cooled to 10° C. in a water-ice bath, which is placed in a 6-liter three-neck flask fitted with a KPG stirrer, inlet and outlet of the inert and a thermometer, and, finally, 148.4 g of 3-methoxyacetophenone (VI) are added (5 minutes). The addition of isopropoxide is slightly exothermic. The resulting temperature of the reaction mixture after addition reaches 35° C. The reaction mixture is then mixed at room temperature for 9 to 10 hours. During the reaction period, the mixture becomes slightly turbid. After said period, 56.6 g of sodium borohydride are slowly and carefully added to the reaction mixture. The duration of this addition is about 2 hours. The reaction mixture thickens into a slurry and foams and it needs to be mixed very intensively. The temperature is kept within the range from 25° C. to 30° C. by mild cooling with ice. If the reaction mixture is overcooled below 20° C. a dense, difficult-to-mix foam forms upon addition of the borohydride. After the borohydride is added, the resulting white slurry is mixed for 10 to 12 hours at room temperature. Then, the supply of the inert is stopped and 800 ml of an aqueous solution of ammonium hydroxide (2:1) are slowly (over 10 minutes) poured into the reaction mixture. The resulting mixture is mixed for 20 minutes. The fine white crystals of the inorganic material are sucked away and well washed with methanol (ca 1 l). The whole alcoholic fraction is evaporated from the filtrate in a rotary vacuum evaporator. The evaporation residue is diluted with 1,000 ml of water and extracted with 3×330 ml of ethylacetate. The combined ethylacetate extract are washed once with 100 ml of water and extracted with 3×200 ml of hydrochloric acid (5:2). The acidic aqueous extracts are combined and alkalized with 20% NaOH (ca 1 l) to pH 12 up to 14 and extracted with 3×300 ml of ethylacetate. The organic fraction is washed with 100 ml of water and 150 ml of brine. It is dried with anhydrous sodium sulfate. The desiccant is filtered off and the filtrate is evaporated to dryness in a rotary vacuum evaporator. The crude product is distilled and ca 60% of the desired product in the form of a colorless oil are obtained. b.p.=68° C. at 400 Pa, 108° C. at 800 Pa

Preparation of 3-(1-dimethylaminoethyl)phenol (IV) According to Literature 3

94 g of [1-(3-methoxyphenyl)ethyl]dimethylamine (V) are dissolved in 285 ml of azeotropic hydrobromic acid and the resulting solution is refluxed under stirring using a reflux condenser for 12 hours (bath temperature 145-150° C.). During boiling, the reaction mixture darkens. The solution is then left to cool down to room temperature. Excess hydrobromic acid is evaporated using a rotary vacuum evaporator and the evaporation residue is dissolved in 200 ml of water. The solution is extracted with 3×100 ml ethylacetate. The aqueous fraction is then gradually alkalized with the saturated solution of sodium carbonate with constant stirring (foam creation). The solution becomes milky turbid and it is extracted with 3×200 ml ethylacetate. The ethylacetate fraction is shaken out 1× with water, 1× with brine and dried with anhydrous magnesium sulfate. Activated carbon is added before filtering off the desiccant and the desiccant along with the carbon are filtered off. The ethylacetate solution of compound (IV) is used for the next step.

Preparation of S-(−)-3-(1-dimethylamino)phenol (III)

Resolving Compound (IV) with an 1 Equivalent Amount of S-(+)-camphor-10-sulfonic Acid A solution of compound (IV) in ethylacetate (0.505 mol)* in 500 ml of ethylacetate) is introduced into a 1-liter round flask with a magnetic stirrer and a solution of S-(+)-camphor-10-sulfonic acid (117.4 g (0.505 mol) in 250 ml of anhydrous ethanol), prepared in warm conditions, is added. The solution is inoculated and left to stand in a refrigerator (+5° C.) overnight. The precipitated crystals are sucked off through fritted glass and left to air dry overnight.

*the contents of compound (IV) was determined by titration 1) 82.2 g of white crystals with m.p.=165-171° C. are obtained, which are dissolved in 190 ml of absolute ethanol under reflux. 380 ml of ethylacetate are added under warm conditions and crystallization is performed according to the above-mentioned procedure.
2) 64.1 g of white crystals with m.p.=174-176° C. are obtained, which are dissolved in 150 ml of ethanol (absol.) under reflux and 300 ml of ethylacetate are added under warm conditions.
3) 56.5 g of white crystals with m.p.=177-179° C. are obtained, which are dissolved in 130 ml of ethanol (absol.) under reflux and 260 ml of ethylacetate are added under warm conditions.
4) 51.6 g of white crystals with m.p.=179-181° C. are obtained; i.e. 25.7% of the theoretical amount.

Resolving Compound (IV) with 0.6 Equivalent Amount of S-(+)-camphor-10-sulfonic Acid 100 g (0.605 mol) of compound (IV) are dissolved in 600 ml of ethylacetate under stirring and reflux. A solution of S-(+)-camphor-10-sulfonic acid (84.3 g (0.363 mol) in 125 ml of anhydrous ethanol) is added under stirring at 70° C. The solution is inoculated, left to cool down to room temperature under stirring, cooled down with brine to −10 up to −15° C. and it is left to crystallize for at least 12 hours under exclusion of air humidity. The precipitated first fraction of crystals is sucked off and air dried.

1) 95.0 g of white crystals with m.p.=173-175° C. are obtained, which are dissolved in 175 ml of ethanol under stirring and reflux and 350 ml of ethylacetate are added at a temperature of the solution between 60-70° C. The camphorsulfonate will start to crystallize and is left to crystallize at a temperature −5 up to −10° C. for at least 12 hours. The precipitated fraction is sucked off, washed with 2×50 ml of ethylacetate and air dried.
2) 79.5 g of the second fraction with m.p. 176-178° C. are obtained, which are again recrystallized in a mixture of ethanol:ethylacetate (150 ml:300 ml) following the above specified procedure. After being washed with 2×50 ml of ethylacetate, the product is dried freely.
3) 74.6 g of the third fraction with m.p.=177-179° C. are obtained; i.e. 31.0% of the theoretical yield.

Releasing (S)-(−)-3-(1-dimethylamino)phenol (III)

4 l of water were introduced in a 10-1 thick-wall beaker with a KPG stirrer. 250 g of sodium carbonate were added and dissolved under stirring. Crystals of the camphorsulfonate (517.5 g) were added in parts under stirring. When about half of the total amount was added 2 liters of dichloromethane were added. The remainder of the camphorsulfonate was added under constant stirring. The addition period was about 0.5 hour. The resulting mixture was stirred for another 0.5 hour. Then, the layers were separated in a 10-liter separating funnel. The aqueous fraction was extracted with 2×1.5 liter of dichloromethane. The combined organic fractions were extracted with 1.5 liter of water and dried with 600 g of anhydrous sodium sulfate. The desiccant was then filtered off and the filtrate was evaporated until dry. The resulting evaporation residue was then dried in a rotary vacuum evaporator until constant weight at 50° C. and 2,7 kPa.

A white crystalline substance forms (187.0 g; 87%), which is used without purification in the next stage, $[\alpha]_D=-55.7°$; c=1.55, methanol).

The contents of the undesired (R)-enantiomer <0.4%— determined using GC in a chiral column.

Preparation of S-(−)-rivastigmine (II)

300 ml of tetrahydrofuran (THF) are placed in a 0.5 l-three-neck flask and sodium hydride as a 60% dispersion in oil (11.3 g) is added slowly under inert conditions (Ar or $N_2$) and stirring. A suspension develops, to which crystalline compound (III) (46.5 g, 0.281 mol) is added at room temperature. A solution of the phenolate forms, to which 35.7 g (0.281 mol) of carbamoylchloride are added dropwise over 10 minutes while slightly cooling down to 15° C. The reaction is slightly exothermic. The rate of dropping is kept such that the temperature of the reaction mixture does not exceed 30° C. After all the agent is added, the cooling system is put aside and the reaction mixture is mixed for 2 hours at room temperature. Thereafter, THF is evaporated in a rotary vacuum evaporator. The evaporation residue is partitioned between 200 ml 1N NaOH and 500 ml of ether. The organic layer is separated and the aqueous fraction is shaken with additional 2×200 ml of ether. The combined ether layers are shaken out with 1×100 ml water and 1×50 ml brine. The organic fraction is dried over anhydrous sodium sulfate. The solvent is evaporated and the crude product is vacuum distilled.

b.p.=135-140° C. at 13 Pa 45.6 g of a colorless viscous oil are obtained, i.e. a 80.5% yield.

content GC 99.6%

Preparation of S-(+)-rivastigmine hydrogentartrate (I)

45.6 g of S-(−)-rivastigmine and 27.4 g of L-(+)-tartaric acid are dissolved in 125 of anhydrous ethanol at 60-70° C. under stirring. At this temperature, 630 ml of ethylacetate are gradually added to the solution. The solution is left to cool down to room temperature and to crystallize at +5° C. for at least 12 hours. The precipitated white crystalline product is sucked off, washed with 100 ml of ethylacetate, and vacuum dried at 40° C. 67.5 g of the desired product with m.p.=125-126° C. (i.e. 92.6% of the theoretical yield). ($[\alpha]_D=+5.5°$; c=5, ethanol). The contents of the undesired R-enantiomer was less than 0.2% in the sample (capillary electrophoresis).

Preparation of S-(−)rivastigmine (II)

150 ml of diethylether are placed in a 0.5 l-three-neck flask and sodium hydride as a 60% dispersion in oil (0.48 g) is added slowly under inert conditions (Ar or $N_2$) and stirring. A suspension develops, to which crystalline compound (III) (2.0 g, 0.012 mol) is added at room temperature. After stirring for one hour, a slightly turbid solution of the phenolate forms, to which 1.53 g (0.012 mol) of N-ethyl-N-methylcarbamoylchloride in 20 ml of ether are added dropwise at room temperature. The resulting reaction mixture is stirred at room temperature for 3 hours. Thereafter, it is diluted with 100 ml of water. The organic layer is separated and extracted with 2×50 ml of a 0.1 N NaOH solution. The organic phase is extracted with 50 ml of water, dried with anhydrous magnesium sulfate, and concentrated in vacuo. 2.6 g of an oil are obtained (86.6% of the theoretical yield).

Preparation of S-(−)rivastigmine (II)

50 ml 1,2-dimethoxyethane are placed in a 0.25 l round three-neck flask and compound (III) (2.0 g, 0.012 mol) is dissolved therein under stirring and under an inert (Ar or $N_2$) at room temperature. Then, a 1.6M solution of n-butyllithium in hexane (7.5 ml) is added dropwise to the resulting solution. A slightly turbid solution of the phenolate develops, to which 1.53 g (0.012 mol) of N-ethyl-N-methylcarbamoylchloride in 20 ml of 1,2-dimethoxyethane are added dropwise at room temperature. The solvent is evaporated in a rotary vacuum evaporator. The evaporation residue is partitioned between 20 ml 1N NaOH and 50 ml of ether. The organic layer is separated and the aqueous fraction is shaken with additional 2×20 ml of ether. The combined ether layers are shaken with 1×20 ml water and 1×20 ml brine. The organic fraction is dried over anhydrous sodium sulfate and concentrated in vacuo. 1.56 g of an oil are obtained (51.5% of the theoretical yield).

Preparation of S-(+)-rivastigmine hydrogentartrate (I)

2.0 g of base (II) and 1.2 g of L-(+)-tartaric acid are dissolved in 5 ml of methanol at 60° C. The clear solution is left to cool down to room temperature and it is gradually precipitated with acetone (ca 50 ml). The resulting mixture is left to crystallize at +5° C. overnight. The deposited crystals are sucked off using fritted glass and washed with acetone. They are dried in vacuo at 40° C. and 2.4 g of white crystals (80% of the theoretical yield) with m.p.=123-5° C. are obtained.

The obtained results differed according to the used method of resolving substance IV. The method with 1 equivalent amount of (S)-(+)-camphor-10-sulfonic acid provided a total yield of 16.2% based on compound IV and that with 0.6 equivalent provided a total yield of 19.5% based on compound IV.

LITERATURE

1) Stedman E, Stedman E.: J. Chem. Soc. 613 (1929)
2) Bhattacharyya, Sukanta: J. Org. Chem. 60; 15; 4928-4929 (1995)
3) Stedman; Stedman: J. Chem. Soc. 613, (1929)
4) MacDonald J.; Stedman E.: J. Chem. Soc. 2513, (1932)

The invention claimed is:

1. A method of production of (−)-(S)-3-[1-(dimethylamino)ethyl]phenyl-N-ethyl-N-methylcarbamate, of formula II

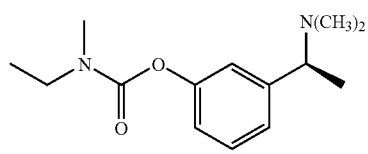

or of its hydrogentartrate of formula I

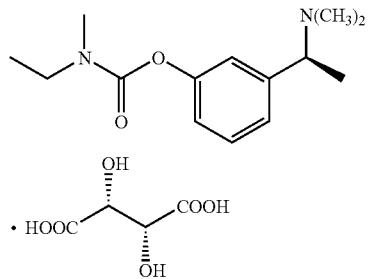

comprising, reductively aminating methoxyacetophenone of formula VI

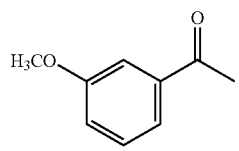

to form the compound of formula V

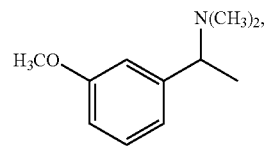

which is thereafter O-dealkylated to the racemic amine of formula IV

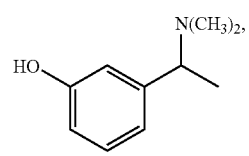

which is further resolved by reacting with (S)-(+)-camphor-10-sulfonic acid, whereafter the desired respective diastereoisomer is crystallized and finally converted into the compound of formula III

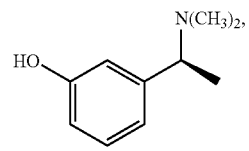

which, in turn, is reacted, optionally in the form of its alkali salt, with a compound of formula VII

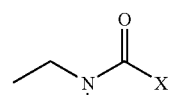

wherein X is a leaving group to produce (−)-(S)-3-[1-(dimethylamino)ethyl]phenyl-N-ethyl-N-methylcarbamide.

2. The method according to claim 1, wherein the racemic amine of formula IV is resolved by reacting with 1 equivalent of (S)-(+)-camphor-10-sulfonic acid.

3. The method according to claim 1, wherein the racemic amine of formula IV is resolved by reacting with 0.6 equivalent of (S)-(+)-camphor-10-sulfonic acid.

4. The method according to claim 1, wherein the obtained desired respective diastereoisomer is further re-crystallized.

5. The method according to claim 4, wherein the obtained desired respective diastereoisomer is further re-crystallized from ethylacetate, optionally in admixture with ethanol.

6. The method according to claim 1, wherein the obtained desired respective diastereoisomer is further re-crystallized.

7. The method according to claim 2, wherein the obtained desired respective diastereoisomer is further re-crystallized.

8. The method according to claim 3, wherein the obtained desired respective diastereoisomer is further re-crystallized.

9. The method according to claim 6, wherein the obtained desired respective diastereoisomer is further re-crystallized from ethylacetate, optionally in admixture with ethanol.

10. The method according to claim 7, wherein the obtained desired respective diastereoisomer is further re-crystallized from ethylacetate, optionally in admixture with ethanol.

11. The method according to claim 8, wherein the obtained desired respective diastereoisomer is further re-crystallized from ethylacetate, optionally in admixture with ethanol.

* * * * *